(12) United States Patent
Sinkus et al.

(10) Patent No.: US 6,833,703 B2
(45) Date of Patent: Dec. 21, 2004

(54) MECHANICAL OSCILLATOR FOR MR ELASTOGRAPHY

(75) Inventors: Ralph Sinkus, Hamburg (DE); Michael Wilhelm Paul Dargatz, Hamburg (DE); Christiane Kuhl, Bonn (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/295,395

(22) Filed: Nov. 15, 2002

(65) Prior Publication Data

US 2003/0128033 A1 Jul. 10, 2003

(30) Foreign Application Priority Data

Nov. 15, 2001 (DE) .......................................... 101 56 178

(51) Int. Cl.[7] .................................................. G01V 3/00
(52) U.S. Cl. ...................................................... 324/318
(58) Field of Search ............................... 324/307–309, 324/318; 600/410, 415, 417, 421, 587, 422, 425; 128/653.5; 250/363.02

(56) References Cited

U.S. PATENT DOCUMENTS

| | | | | |
|---|---|---|---|---|
| 4,691,163 A | * | 9/1987 | Blass et al. .................. | 324/318 |
| 5,363,845 A | * | 11/1994 | Chowdhury et al. ......... | 600/422 |
| 5,490,513 A | * | 2/1996 | Damadian et al. ........... | 600/415 |
| 5,519,221 A | * | 5/1996 | Weinberg .............. | 250/363.02 |
| 5,534,778 A | * | 7/1996 | Loos et al. .................. | 324/318 |
| 5,569,266 A | * | 10/1996 | Siczek ......................... | 606/130 |
| 5,595,177 A | * | 1/1997 | Mena et al. ................. | 600/429 |
| 5,623,927 A | * | 4/1997 | Damadian et al. ........... | 600/415 |
| 5,664,569 A | * | 9/1997 | Damadian et al. ........... | 600/421 |
| 5,678,549 A | * | 10/1997 | Heywang-Koebrunner et al. ........................... | 600/417 |
| 5,699,802 A | * | 12/1997 | Duerr ......................... | 600/422 |
| 5,804,969 A | * | 9/1998 | Lian et al. ................... | 324/318 |
| 5,825,186 A | * | 10/1998 | Ehman et al. ............... | 324/309 |
| 5,833,633 A | * | 11/1998 | Sarvazyan ................... | 600/587 |
| 5,855,554 A | * | 1/1999 | Schneider et al. ........... | 600/407 |
| 5,860,934 A | * | 1/1999 | Sarvazyan ................... | 600/587 |
| 5,899,865 A | * | 5/1999 | Chance ........................ | 600/473 |
| 5,952,828 A | | 9/1999 | Rossman et al. | |
| 5,965,891 A | * | 10/1999 | Weinberg .............. | 250/363.02 |
| 6,023,166 A | * | 2/2000 | Eydelman .................... | 324/318 |
| 6,037,774 A | | 3/2000 | Felmlee et al. | |
| 6,161,034 A | * | 12/2000 | Burbank et al. ............. | 600/431 |
| 6,229,145 B1 | * | 5/2001 | Weinberg .............. | 250/363.02 |
| 6,254,614 B1 | * | 7/2001 | Jesseph ....................... | 606/130 |
| 6,377,836 B1 | * | 4/2002 | Arakawa et al. ............ | 600/422 |
| 6,486,669 B1 | * | 11/2002 | Sinkus et al. ............... | 324/307 |
| 6,493,572 B1 | * | 12/2002 | Su et al. ...................... | 600/422 |
| 6,545,280 B2 | * | 4/2003 | Weinberg .............. | 250/363.02 |
| 6,569,176 B2 | * | 5/2003 | Jesseph ....................... | 606/167 |
| 6,618,608 B1 | * | 9/2003 | Watkins et al. ............. | 600/412 |
| 6,620,115 B2 | * | 9/2003 | Sarvazyan et al. .......... | 600/587 |
| 6,675,037 B1 | * | 1/2004 | Tsekos ........................ | 600/417 |

* cited by examiner

Primary Examiner—Diego Gutierrez
Assistant Examiner—Dixomara Vargas
(74) Attorney, Agent, or Firm—Thomas M. Lundin

(57) ABSTRACT

The invention relates to a mammography accessory for MR elastography which is capable of generating longitudinal oscillations which extend in the longitudinal direction in the mammae of a patient to be examined. The examination time can thus be reduced while at the same time realizing a rendition of the mammae in transverse slice images which is acceptable to examiners.

14 Claims, 3 Drawing Sheets

MECHANICAL OSCILLATOR FOR MR ELASTOGRAPHY

BACKGROUND

The invention relates to a mammography accessory for MR elastography (MR=magnetic resonance), as well as to an MR apparatus equipped with a mammography accessory of this kind.

MR elastography utilizes the fact that the phase in an MR image of the object to be examined changes under the influence of mechanical waves acting on the object to be examined. The extent of this change is dependent on the deflection (that is, the shift out of the state of equilibrium) of the tissue that is caused by the mechanical waves. Information concerning given mechanical parameters of the tissue, for example, concerning the elasticity, can thus be derived from the MR phase images, that is, images reproducing the phase of the nuclear magnetization.

Mammography is a preferred field of application of MR elastography, that is, the imaging of the breast (mamma). A mammography accessory which is suitable for this purpose is known from U.S. patent application Ser. No. 09/743,659 in which mechanical waves are excited in the mamma by an oscillation applicator which oscillates horizontally and perpendicularly to the longitudinal direction of the patient to be examined. A drawback in this respect is the long duration of the examination performed by means of such an accessory (up to 30 minutes). An arrangement as disclosed in U.S. Pat. No. 5,952,828 has a similar drawback. The oscillation applicators then act from below on the mammae of the patient in the prone position, thus producing an oscillation tangentially to their contact surface. However, in essence only transverse waves are excited in the mammae; such transverse waves, however, have a penetration depth which is less than that of longitudinal waves.

SUMMARY

It is an object of the present invention to provide a mammography accessory which is suitable for reducing the examination time and excites predominantly longitudinal mechanical waves in the mammae.

This object is achieved in accordance with the invention by means of a mammography accessory for elastography which includes a positioning unit which is provided with a supporting surface in which at least one opening is formed so as to receive at least one of the mammae and also includes an oscillation generating arrangement for generating mechanical waves via at least one oscillation applicator which performs a reciprocating motion in the longitudinal direction of a patient to be examined and has a contact surface which extends at least approximately perpendicularly to its oscillation direction.

Like in the known mammography accessories, the mammae are compressed to a given extent in the direction perpendicular to the contact surface of the oscillation applicators. However, whereas in the known accessories the compression causes an increase of the dimensions of the mammae in the longitudinal direction of the patient, the compression of the mammae in accordance with the invention causes a decrease of these dimensions because the contact surface has an effect in this direction. The imaging of the mammae by forming a number of slice images in the direction perpendicular to the longitudinal direction (this orientation of the slice images is necessary to enable simultaneous imaging of the breast wall and the axillary areas) requires a smaller number of slices and hence a shorter period of time for the acquisition of the MR data required for these slices.

A further advantage resides in the fact that the mammae appear in substantially non-distorted form in the individual slice images when this direction of compression is employed. In the case of the known mammography accessories, however, the mammae appear in these slice images so as to be distorted from the side or from below; this impedes the diagnosis and is not acceptable to many examiners.

One embodiment of the invention enables adaptation to different anatomical circumstances. The compression may then be chosen to be such that on the one hand the mamma is fixed but on the other hand it can still be elastically deformed. A further embodiment enables the fixation of the mammae also at the side of the oscillation applicator. The oscillation applicator itself may then be stationary relative to the positioning unit.

The positioning unit may in principle have a comparatively wide opening for receiving both mammae. Another embodiment, however, offers the advantage that each mamma can be enclosed by an MR receiving coil, thus enabling undisturbed reception of the MR signals. Moreover, the adjacently arranged MR receiving coils enable SENSE measurements so that the examination time is reduced even further.

In order to carry out MR elastography the magnetic gradient fields act on the examination zone simultaneously with the mechanical waves. This is achieved by means of an MR apparatus that includes the subject accessory.

In accordance with one aspect of the invention, a mammography accessory for MR elastography is provided. The accessory includes a positioning unit which is provided with a supporting surface in which at least one opening is formed so as to receive at least one of the mammae, and also includes an oscillation generating arrangement for generating mechanical oscillations via at least one oscillation applicator which performs a reciprocating motion in the longitudinal direction of a patient to be examined and has a contact surface which extends at least approximately perpendicularly to its oscillation direction.

In accordance with a more limited aspect of the present invention, the mammography accessory includes a first compression plate which is arranged at the side of the opening which faces the oscillation applicator and is adjustable in the oscillation direction of the oscillation applicator.

In accordance with a more limited aspect of the invention, the mammography accessory includes a second compression plate which is arranged at the side of the opening which faces the first compression plate, which is mounted so as to be stationary relative to the positioning unit and through which the oscillation applicator acts on the zone between the two compression plates.

In accordance with a more limited aspect of the invention, the mammography accessory includes two openings for a respective mamma, at the area of each opening there being provided at least one MR coil which is situated in a plane parallel to the supporting surface and serves to receive MR signals, and also an oscillation applicator which forms part of the oscillation generating arrangement.

In accordance with another aspect of the invention, an MR apparatus is provided. The MR apparatus includes a mammography accessory as described herein and also includes a generator which controls the variation in time of magnetic gradient fields, and a control unit which controls the generator and the mammography accessory in such a manner that the mechanical oscillations generated by the mammography accessory and the magnetic gradient fields are synchronized relative to one another.

DRAWINGS

The invention will be described in detail hereinafter, by way of example, with reference to the drawings. Therein:

DESCRIPTION

Figure 1:
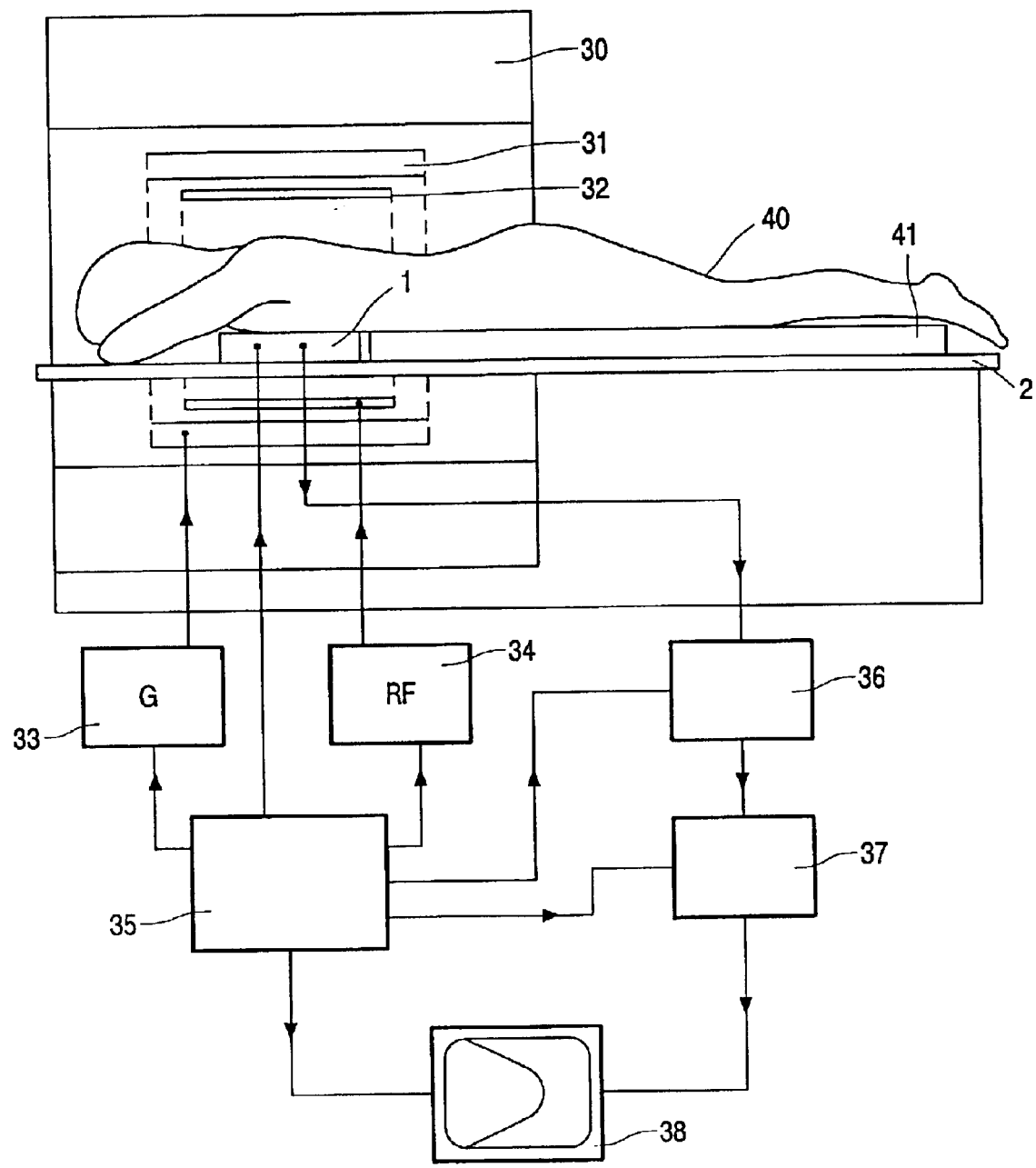
FIG. 1 shows an MR apparatus provided with a mammography accessory.

FIG. 1 is a diagrammatic cross-sectional view of an MR apparatus and the circuitry and software components required for the operation thereof. The MR apparatus includes a main field magnet 30 for generating a main field B0 which extends horizontally and parallel to the plane of drawing in FIG. 1. Inside this cylindrical main field magnet there is arranged a set 31 of gradient coils for generating magnetic fields having gradients in three mutually perpendicular directions. Inside these gradient coils there is arranged an RF coil 32 for generating an RF magnetic field.

The currents for the gradient coils 31 are supplied by a generator 33 whereas the currents for the RF coil 32 are supplied by an RF generator 34. The variation in time of the currents generated by the generators 33 and 34 is controlled by a control unit 35. The MR signals generated in the examination zone are received by an MR receiver 36 and prepared so as to be applied to an image processing unit 37 which reconstructs an MR image from the MR signals received, which MR image is displayed on a monitor 38.

In the examination zone defined by the coils 31 and 32 there is arranged a patient 40 who is positioned on a cushion 41 resting on a patient table 2. In front of the cushion 41 there is arranged a mammography accessory 1 which has a similar height as the cushion 41.

Figure 2:
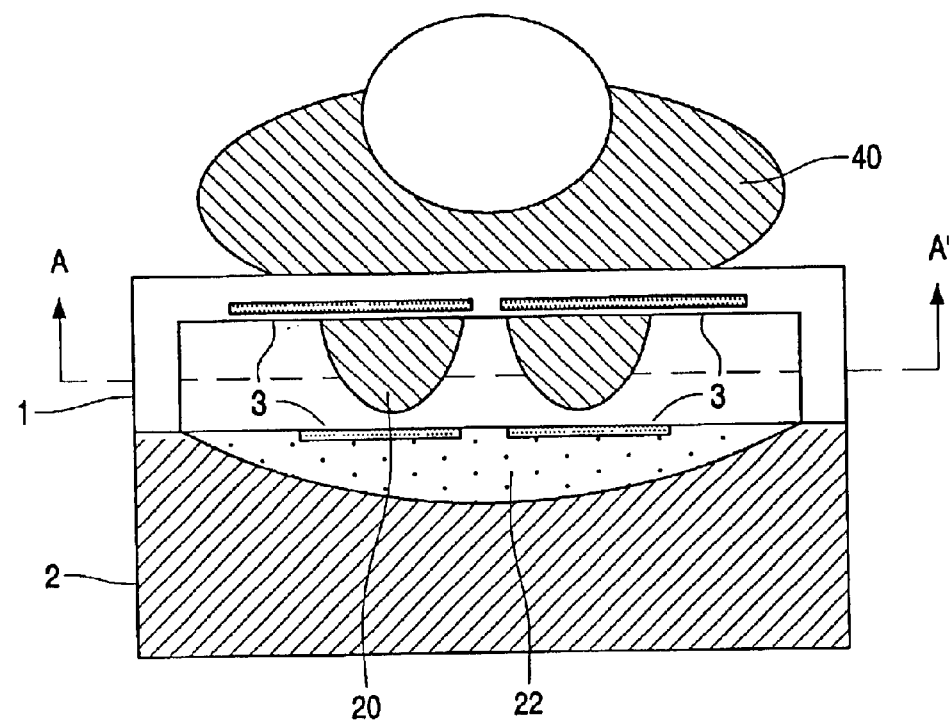
FIG. 2 shows the mammography accessory in a sectional plane perpendicular to the longitudinal direction.
Figure 3:
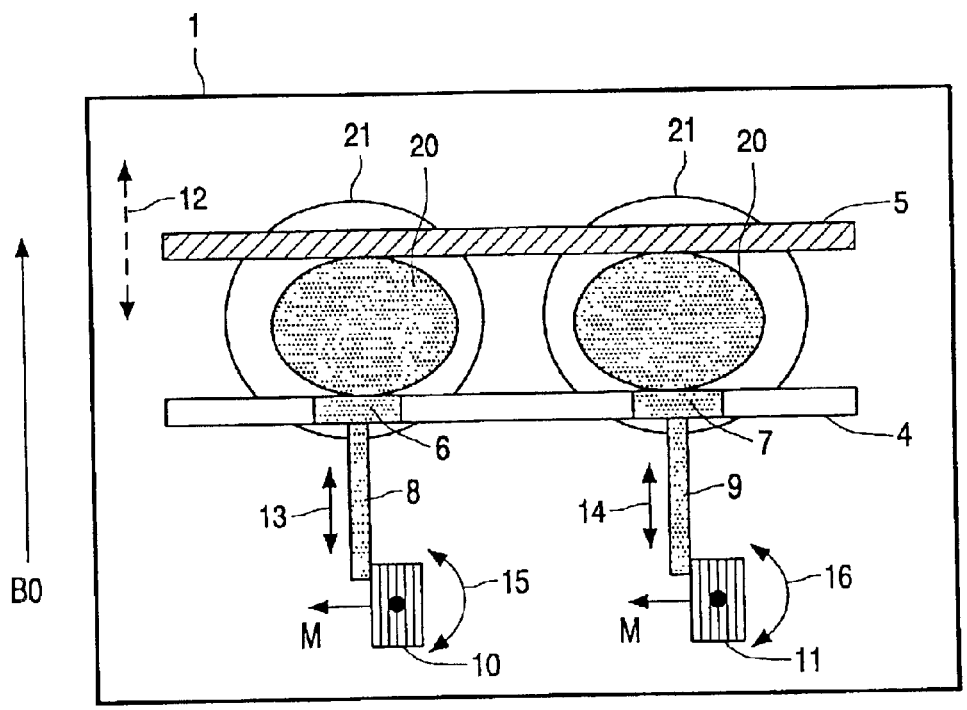
FIG. 3 is a detailed view taken along the line A-A' in FIG. 2, and FIGS. 4a and 4b compare the effect of the accessory in accordance with the invention with that of the known mammography accessory.

The mammography accessory is shown in greater detail in the FIGS. 2 and 3. FIG. 2 shows this accessory in a vertical sectional plane perpendicular to the plane of drawing of FIG. 1 whereas FIG. 3 is a view from below, that is, a view taken along the line A-A' in FIG. 2. For the sake of simplicity, some components are shown in only one of the two Figs.

As is shown in FIG. 2, the mammography accessory includes a bridge-like positioning unit 1 whose upper surface constitutes a supporting surface for the patient resting thereon in the prone position. The supporting surface is provided with two adjoining openings wherethrough the mammae 20 of the patient 40 can hang down without obstruction. The positioning unit is closed at the bottom side by a member 22 of a synthetic material whose outer contour is adapted to the concave shape of the top 2 of the patient table situated therebelow.

Two coils 3 are situated in the upper and the lower zone of the mammography accessory, that is, in horizontal planes; the upper coils are integrated in the supporting surface and the lower coils in the member 22 of a synthetic material. This arrangement gives rise to a uniform spatial sensitivity profile of the coils. The coil pair associated with each mamma is connected to a common receiving channel. Because the sensitivity profiles of the adjacently situated coils overlap, moreover, SENSE measurements can be performed in the right-left direction, resulting in an additional gain in respect of time.

As is shown in FIG. 3, inside the mammography accessory there are provided two compression plates 4 and 5 which extend in planes perpendicular to the longitudinal direction of the patient table and underneath the openings. The compression plate 4 is connected to the positioning unit 1 whereas the compression plate 5 is adjustable, by way of a mechanical system which is not shown, in the directions towards the compression plate 4 and away therefrom. The compression can thus be individually adapted to the anatomy of the patient in question.

Moreover, the positioning unit is provided with two oscillation generators, each of which includes an oscillation applicator. Each oscillation applicator comprises a head 6, 7 provided with a contact surface which extends perpendicularly to the longitudinal direction of the table, and also a piston 8, 9, respectively, which is connected thereto and extends in the longitudinal direction of the table. Each piston performs a reciprocating oscillatory motion in the direction of the arrows 13, 14, respectively, that is, in its longitudinal direction, so that the heads 6, 7 act on the mammae 20 via a respective opening in the compression plate 4. The oscillatory motion is produced by means of a drive coil 10, 11, respectively, which is journaled so as to be pivotable about a vertical axis and conducts an alternating current so that the pivoting motions as represented by the arrows 15 and 16 are induced in the main magnetic field B0 of the magnet, said motions being transmitted to the oscillation applicator 6, 8 and 7, 9, respectively.

The function of the mammography accessory will be described in detail hereinafter in relation to an MR elastography examination.

After the patient 40 has been positioned in conformity with FIG. 1, the compression plate 5 is displaced so as to realize a slight compression which suffices to fix the mammae but is not so strong that the mammae are no longer elastically deformable. This compression increases the width of the mammae in the right-left direction and compresses the mammae in the foot-head direction.

Subsequently, the control unit 35 initiates an alternating current of a frequency of, for example, 200 Hz in the drive coils 10, 11, so that predominantly longitudinal waves of this frequency are excited in the mammae 20; such waves can very well penetrate the mammae. Subsequently, the MR sequences required for the acquisition of the necessary MR data are generated. The nuclear magnetization is then excited in transverse slices (slices perpendicular to the longitudinal direction) in the mammae. The excitation of the nuclear magnetization in an individual slice then involves the generating of at least one RF pulse by the RF coil 32 and the RF generator 34 in conjunction with a gradient of the magnetic field which is induced by the gradient coil system 31 in conjunction with the generator 33 and extends in the longitudinal direction of the magnetic field, so that the nuclear magnetization is excited in a slice perpendicular to the longitudinal direction. This nuclear magnetization is phase encoded by a further magnetic field gradient. Before the MR signal is read out, a preferably sinusoidally varying, periodic, gradient magnetic field acts on the examination zone, the period of said gradient magnetic field being synchronized with the period of the mechanical waves by the control device 35.

The foregoing is repeated for further slices until the mammae have been completely covered in parallel slices.

The excitation of the nuclear magnetization in transverse slices is then repeated while using other phase codes, until a sufficient amount of MR data has been acquired for a complete image of the slice. This imaging method is repeated a number of times while changing the relative position in time of the mechanical oscillation and the sinusoidal gradient oscillation. The overall cycle is then repeated two more times with a changed orientation of the sinusoidally varying magnetic field. It will be evident that such an examination requires a comparatively large amount of time.

Figure 4A:
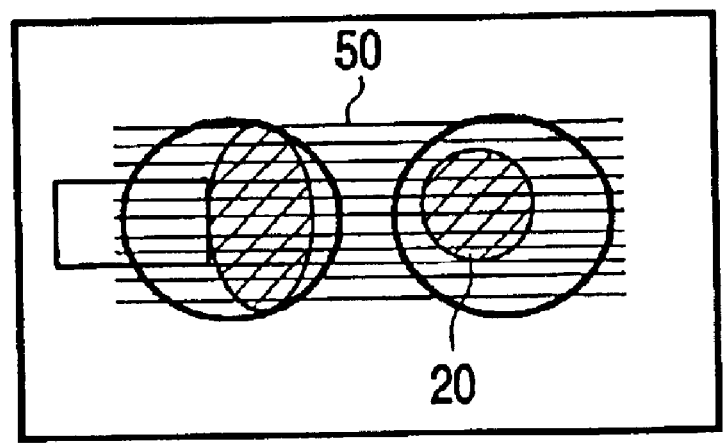

The examination time is dependent on the number of transverse slices whereby the mammae can be covered. The mammography accessory in accordance with the invention reduces the number of slices and hence the examination time. This is illustrated in the FIGS. 4a and 4b. FIG. 4a shows the situation in the known mammography accessory as disclosed in U.S. patent application Ser. No. 09/743,659. The mammae are then compressed in the right-left direction and expanded in the head-foot direction. Consequently, a comparatively large number of slices 50 is required for complete imaging of the mammae.

Figure 4B:
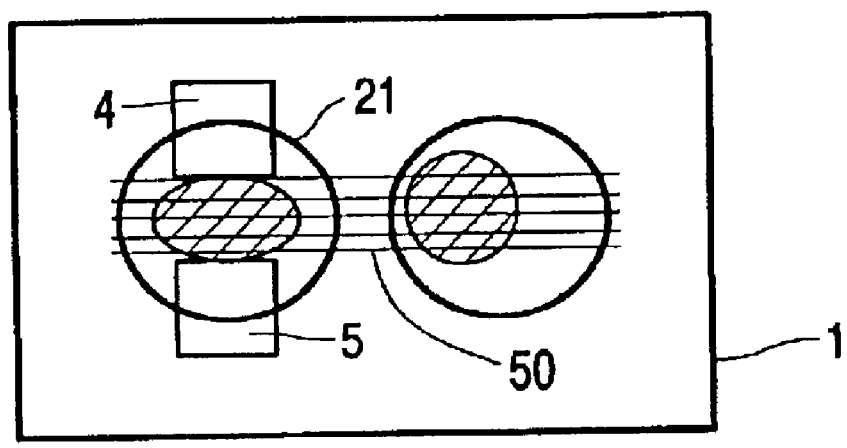

FIG. 4b, however, shows the situation in accordance with the invention. The mammae are compressed in the head-foot direction and expanded in the right-left direction. The number of slice images required for complete imaging, therefore, is smaller than in the known method; consequently, the time required for the examination is proportionally shorter. Because the compression takes place perpendicularly to the slice planes, the shape of the mamma is maintained to a high degree in the individual slice images, whereas the deformation in the direction of the slice in conformity with FIG. 4a yields an image which is not acceptable to many examiners.

The mammography accessory in accordance with the invention can also be advantageously used for high-resolution dynamic MR mammography in which the mammae are imaged by means of a suitable contrast agent which contains, for example, gadolinium. The measuring time is reduced also in this case. Furthermore, it is advantageous that the compression plates 4 and 5 fix the mammae so that motional artefacts are avoided.

Both methods, that is, dynamic MR mammography and MR elastography, can also be carried out in combination during an examination of the mammae. First dynamic MR mammography is then carried out and the zone thus recognized as the zone of interest for the diagnosis is subsequently examined by means of MR elastography.

It is not necessary for the contact faces of the heads 6, 7 to extend exactly perpendicularly to their direction of oscillation. In order to ensure that the oscillation generator excites essentially longitudinal waves in the mammae, however, it is important that the contact surfaces intersect the direction of oscillation at an angle other than 0°.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. A mammography accessory for MR elastography which includes a positioning unit which is provided with a supporting surface in which at least one opening is formed so as to receive at least one mammae, and also includes an oscillation generating arrangement for generating mechanical oscillations via at least one oscillation applicator which performs a reciprocating motion in the longitudinal direction of a patient to be examined and has a contact surface which extends at least approximately perpendicularly to its oscillation direction and which includes two openings for a respective mamma, at the area of each opening there being provided at least one MR coil which is situated in a plane parallel to the supporting surface and serves to receive MR signals, and also an oscillation applicator which forms part of the oscillation generating arrangement.

2. A mammography accessory as claimed in claim 1, which includes a first compression plate which is arranged at the side of the opening which faces the oscillation applicator and is adjustable in the oscillation direction of the oscillation applicator.

3. A mammography accessory as claimed in claim 2, which includes a second compression plate which is arranged at the side of the opening which faces the first compression plate, which is mounted so as to be stationary relative to the positioning unit and through which the oscillation applicator acts on the zone between the two compression plates.

4. A magnetic resonance apparatus comprising:
   a main field magnet for generating a main magnetic field in an examination region;
   a plurality of gradient coils for generating magnetic field gradients in the examination region in slice, phase, and read encode directions;
   an RF transmit coil for exciting magnetic resonance in a subject disposed within the examination region;
   an RF receive coil for receiving magnetic resonance signals from the subject;
   a plurality of compression members, disposed in the examination region, for compressing a portion of interest of the subject in substantially the slice encode direction; and
   an oscillation applicator for generating oscillations substantially in the slice encode direction in the portion of interest, the oscillation applicator having an application surface which contacts the portion of interest and intersects an axis defined by the slice encode direction.

5. A magnetic resonance apparatus according to claim 4 wherein the subject has a longitudinal axis and the longitudinal axis is substantially parallel to the slice encode direction.

6. A magnetic resonance apparatus according to claim 4, further comprising:
   a control unit which controls the gradient coils and the oscillation applicator such that the oscillations and the magnetic field gradients are synchronized relative to one another.

7. A magnetic resonance apparatus according to claim 4, wherein the RF receive coil comprises a coil pair disposed around the portion of interest.

8. A magnetic resonance apparatus according to claim 4, wherein the application surface is substantially perpendicular to the slice encode direction.

9. A magnetic resonance apparatus according to claim 4, wherein the portion of interest is a mamma.

10. A magnetic resonance method comprising the steps of:
   generating a main magnetic field in an examination region;
   generating magnetic field gradients in slice, phase, and read encode directions within the examination region;

compressing a portion of interest of a subject disposed within the examination region, the portion of interest being compressed in substantially the slice encode direction;

inducing oscillations in the portion of interest substantially in the slice encode direction;

transmitting RF signals into the examination region to excite magnetic resonance in the portion of interest; and receiving RF signals from the portion of interest.

11. A magnetic resonance method according to claim 10 wherein the oscillations are induced using an oscillation applicator, the oscillation applicator comprising an application surface which contacts the portion of interest and intersects an axis defined by the slice encode direction.

12. A magnetic resonance method according to claim 11 wherein the application surface is substantially perpendicular to the slice encode direction.

13. A magnetic resonance method according to claim 12 wherein the subject defines a longitudinal axis and the longitudinal axis is substantially parallel with the slice encode direction.

14. A magnetic resonance method according to claim 11 further comprising synchronizing the oscillations and the magnetic field gradients.

* * * * *